(12) United States Patent
Pirrung et al.

(10) Patent No.: US 6,294,659 B1
(45) Date of Patent: Sep. 25, 2001

(54) PHOTOCLEAVABLE NUCLEOSIDE BASE AND NUCLEIC ACIDS INCLUDING

(75) Inventors: Michael C. Pirrung, Chapel Hill, NC (US); Xiadong Zhao, Piscataway, NJ (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/353,584

(22) Filed: Jul. 15, 1999

Related U.S. Application Data
(60) Provisional application No. 60/092,963, filed on Jul. 15, 1998.

(51) Int. Cl.[7] .......................... C07H 21/00; C07H 21/02; C07H 21/04
(52) U.S. Cl. ................ 536/23.1; 536/25.32; 536/25.33; 536/29.2
(58) Field of Search ................ 536/23.1, 25.32, 536/25.33, 29.2

(56) References Cited

U.S. PATENT DOCUMENTS 5,438,131 * 8/1995 Bergstrom et al. ............. 536/28.6
5,738,993 * 4/1998 Fugono et al. ..................... 435/6
6,011,143 * 1/2000 Shionoya et al. .............. 536/23.1

OTHER PUBLICATIONS

Liu et al., "The Structure of Chicanine, a New Lignan from *Schisandra sp.*," *Canadian Journal of Chemistry*, 59(11), 1680–1684 (1981); *Chemical ABstracts*, 95, Abstract No. 111711p (Sep. 28, 1981); only abstract supplied.*

Huang et al., "Structure of En Shi Zhi Su, a New Lignan from *Schisandra henryi Clarke*, "*Zhongcaoyao*,13(2), 22 (1982); 97, Abstract No. 107029w (Sep. 27, 1982); only abstract supplied.*

Kurihara et al., "Synthesis and Biological Activity of 3–Quinolineacetic acid Derivatives," *Yakugaku Zasshi*, 98(6), 802–816 (1978); *Chemical Abstracts*, 90, Abstract No. 6216e (Jan. 1, 1979); only abstract supplied.*

\* cited by examiner

*Primary Examiner*—Gary Geist
*Assistant Examiner*—L. E. Crane
(74) *Attorney, Agent, or Firm*—Nixon & Vanderhye P.C.

(57) ABSTRACT

The present invention relates, in general, to a nucleoside base and, in particular, to a universal, photocleavable nucleoside base. The invention further relates to oligonucleotides comprising such a base.

4 Claims, 3 Drawing Sheets

A C G T Ns

P+4 →

P+1 →
P →

Lane 1 2 3 4 5 6 hv         −   +   +
Piperidine −   −   +

← 25

← 12-P

Lane  1   2   3

PHOTOCLEAVABLE NUCLEOSIDE BASE AND NUCLEIC ACIDS INCLUDING

This application claims priority from Provisional Application No. 60/092,963, filed Jul. 15, 1998, the disclosure of which is incorporated herein by reference.

This invention was made with U.S. Government support under Grant No. 95-08-0023 awarded by the National Institute of Standards and Technology, Advanced Technology Program. The U.S. Government has certain rights in the invention.

TECHNICAL FIELD

The present invention relates, in general, to a nucleoside base and, in particular, to a universal, photocleavable nucleoside base. The invention further relates to oligonucleotides comprising such a base.

BACKGROUND

A variety of novel techniques for analysis of nucleic acids best utilize relatively short, single-stranded analytes. Many such techniques are based on the hybridization of analyte nucleic acids to miniaturized arrays of short (<25 nucleotides), single-stranded DNA probes (Ramsay, Nat. Biotechnol. 16:40 (1998); Marshall et al, J. Nat. Biotechnol. 16:27 (1998)). Samples of analyte DNA often arise by PCR amplification from a biological sample, range from hundreds to thousands of nucleotides and are obtained as double-stranded molecules. As hybridization requires single-stranded nucleic acids, various means have been devised to render amplification products single-stranded.

The stability of duplex nucleic acid is directly proportional to molecular length. Thus, it can be difficult to form single-stranded analytes from long, double-stranded amplicons. Further, it has been observed in some instances that the performance of various nucleic acid analysis techniques, such as the above-referenced array-based methods, is superior with shorter analyte nucleic acids. This has created a demand for methods of fragmenting analyte nucleic acid or amplification products thereof.

Available fragmentation methods include limited restriction digestion of the amplicon, as well as the incorporation of uridine during amplification followed by backbone cleavage using uracil-N-glycosylase. These methods, however, have drawbacks related to their a sequence bias and the additional processing steps needed to remove reagents/byproducts. Accordingly, there is a clear need for a nucleoside analog that can be enzymatically incorporated at random within a nucleic acid chain and subsequently activated for cleavage of the backbone.

A number of workers have developed analogs of the heterocyclic bases in nucleic acids for various purposes. For example, Bergstrom et al have advanced nitropyrrole and nitroindole as heterocycles that are accepted opposite any of the natural bases in double-stranded nucleic acid (Bergstrom et al, Nucleic Acids Res. 25:1935 (1997); Bergstrom et al, J. Am. Chem. Soc. 117:1201 (1995)). Such "universal" bases have uses including simplified syntheses of short oligonucleotides that are suitable for use as probes for hybridization, and as primers for DNA sequencing and nucleic acid amplification. On the other hand, Kool et al have shown that difluorotoluene specifically substitutes for the base thymidine (T) in duplex DNA with only a small loss in hybrid stability (Schweitzer et al, J. Org. Chem. 59:7238 (1994)). Further, difluorotoluene is accepted by DNA polymerases either in the template strand or as an incoming triphosphate (Moran et al, Proc. Natl. Acad. Sci. USA 94:10506 (1997); Moran et al, J. Am. Chem. Soc. 119:2056 (1997); Liu et al, Chem. Biol. 4:919 (1997)). As a result, high fidelity complementation of the unnatural base with a natural adenine (A) occurs. Finally, Ordoukhanian et al (J. Am. Chem. Soc. 117:9570 (1995)) have developed unnatural base analogs that can be cleaved into two portions (and thereby cleave the backbone of the nucleic acid) by irradiation. These compounds do not resemble natural nucleosides and are not accepted by nucleic acid modifying enzymes. Thus, they must be incorporated into oligonucleotides by chemical synthesis.

The present invention provides a nucleoside analog that can be enzymatically incorporated into a nucleic acid chain and then activated for cleavage of that chain.

SUMMARY OF THE INVENTION

The present invention relates to a nucleoside base that can be randomly incorporated into newly-synthesized nucleic acid strands by enzymes, and, in a subsequent step, cleaved by UV irradiation, thereby introducing single-strand nicks into double-stranded nucleic acid. Such nicks fragment larger nucleic acids into smaller ones. Because the nicks are random and, therefore, not opposed by nicks on the opposite strand, the average length of uninterrupted double stranded nucleic acid is shortened, facilitating conversion from double-stranded to single-stranded nucleic acid.

Objects and advantages of the invention will be clear from the description that follows.

DETAILED DESCRIPTION OF THE INVENTION

Figure 1:
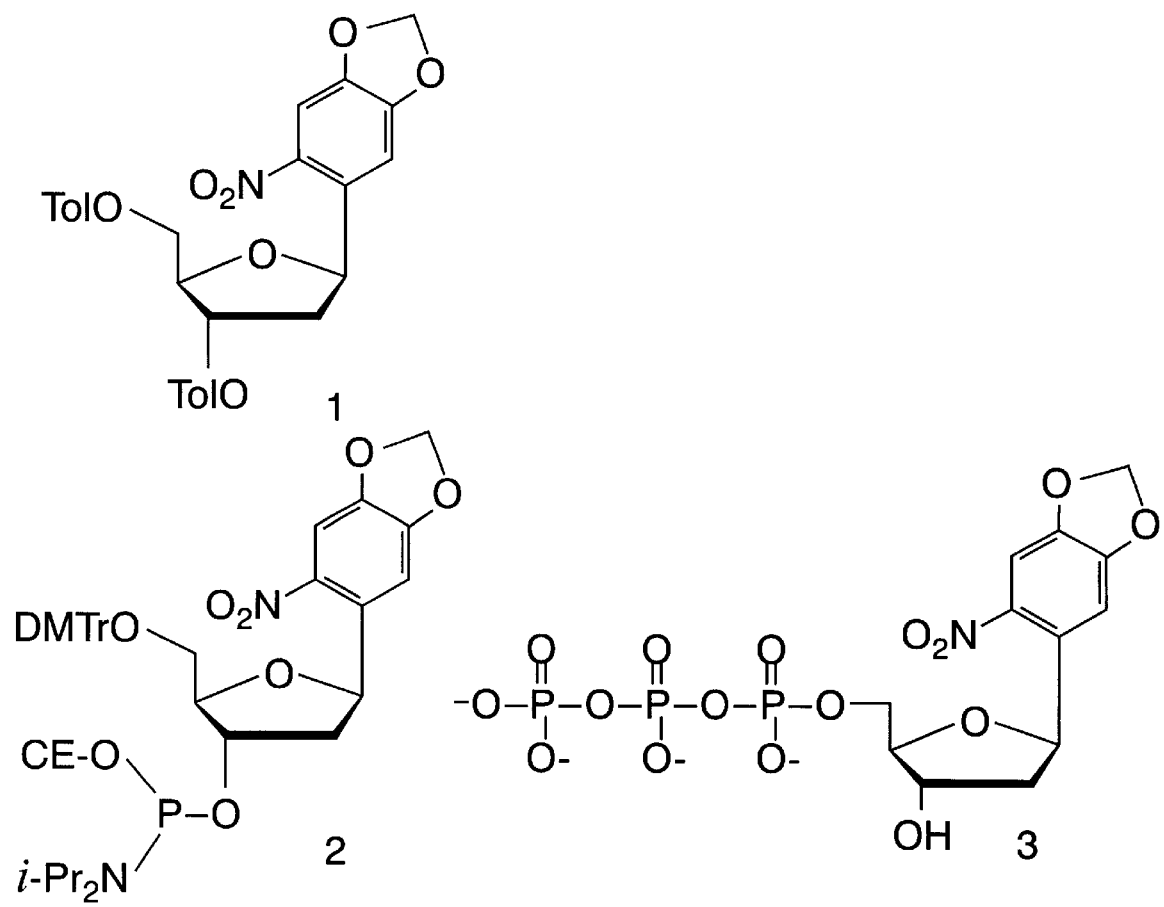
FIG. 1 shows a P★ base-containing nucleoside (derivatized with toluoyl groups) (1), a P★ base-containing 5'-dimethoxytrityl-3'-cyanoethyl(diisopropyl) phosphoramidite (2) and a P★ base-containing nucleoside triphosphate (3).

The present invention relates to a photocleavable, universal nucleoside base (designated the "P★" base), and nucleosides and oligonucleotides comprising same. Nucleosides of the invention comprise the photocleavable P★ base moiety and a sugar moiety and are of the formula

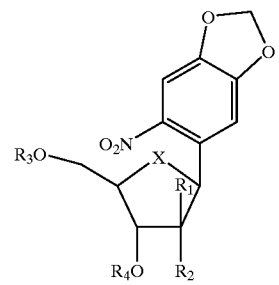

wherein $R_1$ and $R_2$ are, independently, H, OH or $OCH_3$, $R_3$ and $R_4$ are, independently, H, a protecting group (such as a toluoyl moiety), or a mono-, di- or triphosphate, and X is O or S. The nitro-substituted aromatic ring of the P★ base moiety can be further substituted, at any or all available positions on the ring, with, for example, an electron-donating oxygen functionality (e.g., an alcohol or an ether), with a halogen (e.g., F) or with a lower (e.g., $C_1$–$C_4$) alkyl. Most commonly, the sugar moiety of the nucleoside of the invention is D-deoxyribose, as found in naturally occurring deoxyribonucleosides.

Methods of preparing P★ base-containing nucleosides of the invention can be exemplified by the preparation of (nitropiperonyl)deoxyriboside. In that regard, a deoxyribosyl chloride is treated with an aromatic Grignard reagent followed by nitration. Conversion to an H phosphonate or to the 5'-dimethoxytrityl-3'-cyanoethyl(diisopropyl) phosphoramidite can then be effected, for example, for incorporation into oligonucleotides by conventional automated synthesis techniques (see, for example, M. J. Gait, Oligonucleotide Synthesis, IRC Press, Washington, D.C. (1984)). Conversion to the triphosphate can be effected in accordance with the method of Ludwig et al (Org. Chem. 54:631 (1989)) and the resulting triphosphate then enzymatically incorporated into nucleic acids using, for example, E. coli DNA polymerase I or Klenow DNA polymerase. The frequency of incorporation of the P★ base can be varied by altering the concentration of P★ base-containing nucleoside in the reaction mixture.

The effect on hybrid formation when P★ base opposes the four native bases is be small (e.g., <5° C. in melting temperature). Further, P★ base is able to promote incorporation of three native dNTPs (A, G, and T) when in the template strand of a primer-template complex.

Duplexes containing the P★ base can be cleaved by irradiation. Preferably, long wavelength UV irradiation is used (e.g., >350 nm) for a relatively brief period (e.g., about 30 min), followed by base treatment (e.g., with piperidine or $K_2CO_3$, for example, at room temperature, at about 37° C. or at about 95° C.).

The nucleosides of the invention have application in a variety of settings. For example, P★ base-containing nucleosides are particularly suitable for use in the production of oligonucleotides ultimately requiring fragmentation prior to utilization. Since P★ base can be randomly incorporated into newly-synthesized nucleic acids and subsequently activated for cleavage by UV irradiation, it can be used to shorten the average length of uninterrupted double-stranded nucleic acid, thereby facilitating conversion to single-stranded nucleic acids. As indicated above single-stranded nucleic acids can be used in analyses based on hybridization of analyte nucleic acids to single stranded DNA probes, present, for example, in miniaturized arrays.

Certain aspects of the present invention are described in greater detail in the non-limiting Examples that follow.

EXAMPLES

The following experimental details are relevant to the Examples that follow.
Materials and Methods.

$^1$H and $^{31}$P NMR spectra were recorded on GE QE-300 and Varian Inova-400 spectrometers. NOESY were recorded on a Varian Unity 500 MHz spectrometer. Mass spectra were measured on a JEOL-JMS-SX-102 with a FAB/MS source. Infrared spectra were recorded on a BOMEM MB-100 FT-IR spectrometer. Ultraviolet spectra were measured on a Shimadzu UV160U UV-visible spectrophotometer. The melting curves were recorded on an Aviv 62DS spectrophotometer. Melting points were measured on a HAAKE BUCHLER Melting Point Apparatus. Photolysis was performed in a Rayonet Photochemical Reactor. X-ray data were collected on a Siemens SMART diffractometer. High pressure liquid chromatography (HPLC) was carried out on a Hewlett Packard series 1100 with an Alltech C-18 reverse phase column (10 mm×250 mm). T4 polynucleotide kinase and Klenow fragment DNA polymerase were purchased from New England Biolabs. All the reactions were performed under argon atmosphere and freshly distilled anhydrous solvent when it is necessary.

Synthesis
2'-deoxy-1'-piperonyl-3',5'-di-O-toluoyl-D-ribofuranose.

To 5 mL of dry tetrahydrofuran (THF) and magnesium turnings (120 mg, 5 mmol) was added 4-bromo-1,2-methylenedioxybenzene (1.03 g, 5 mmol). The reaction was initiated by adding a few $I_2$ crystals and kept at ~40° C. for 1 hr. $CdCl_2$ powder (450 mg, 2.5 mmol) was added. After refluxing for 1.5 hr, the mixture was cooled to room temperature. 1'α-Chloro-3',5'-di-O-toluoyl-2'-deoxyribose (1.50 g, 3.8 mmol), prepared as reported by Hoffer, was added and stirred over 6 hr. The reaction was quenched with aqueous $NH_4Cl$ and extracted with ethyl acetate. The extract was washed with saturated $NaHCO_3$ solution, saturated NaCl solution and dried over anhydrous $Na_2SO_4$. The products were purified by flash chromatography on silica gel with 12% ethyl acetate in hexane as the eluant. The products (1.60 g, 3.3 mmol) were obtained as a clear oil (epimer α/β, 10:1) at a yield of 87%.

Conversion to 2'-deoxy-1'β-piperonyl-3',5'-di-O-toluoyl-D-ribofuranose.

To 75 mL of toluene were added the α/β epimer mixture (1.00 g) and a catalytic amount of toluenesulfonic acid (100 mg) and one drop of concentrated sulfuric acid and five drops of water. After refluxing for 2 hr, toluene was removed and the residue was neutralized with a $NaHCO_3$ aqueous solution, and extracted with ethyl acetate. The extract was washed with saturated NaCl solution and dried over anhydrous $Na_2SO_4$. The α and β epimers were isolated by flash chromatography on silica gel with 12.5% ethyl acetate in hexane as the eluant. α epimer, 0.30 g (30%)$_3$ $^1$H NMR (300 MHz, $CDCl_3$, ppm, referenced to TMS at 0.00) δ 7.95 (2H, d, J=8.2 Hz), 7.78 (2H, d, J=8.2 Hz), 7.23 (2H, d, J=8.3 Hz), 7.20 (2H, d, J=8.3 Hz), 6.97–6.76 (3H, m), 5.94 (2H, s, $CH_2$), 5.58 (1H, m, H1'), 5.26 (1H, m, H3'), 4.66 (1H, m, H4'), 4.56 (2H, m, H5'5"), 2.89 (1H, m, H2'α), 2.40 (6H, s, 2×$CH_3$), 2.11 (1H, m, H2'β); IR ($CDCL_3$ thin film, $cm^{-1}$), 2922, 2852, 1720, 1271, 1104; β epimer, 0.46 g (46%), $^1$H NMR (300 MHz, $CDCl_3$, ppm, referenced to TMS at 0.00) δ 7.97 (2H, d, J=8.3 Hz), 7.96 (2H, d, J=8.3 Hz), 7.27 (2H, d, J=8.0 Hz), 7.23 (2H, d, J=8.0 Hz), 6.90–6.74 (3H, m), 5.94 (2H, s, $CH_2$), 5.58 (1H, dd, J=1.3, 4.8 Hz, H1'), 5.16 (1H, dd, J=5.0, 10.9 Hz, H3'), 4.63 (2H, m, H5'5"), 4.50 (1H, m, H4'), 2.49 (1H, m, H2'β), 2.44 (3H, S, $CH_3$), 2.41 (3H, s, $CH_3$), 2.22 (1H, m, H2'α); IR ($CDCl_3$ thin film, $cm^{-1}$), 2921, 1719, 1611, 1271, 1105; HRMS (FAB) m/z calcd for $C_{28}H_{26}O_7$ 474.1678, found 474.1682.

2'-deoxy-1'β-nitropiperonyl-3',5'-di-O-toluoyl-D-ribofuranose.

To a 175 mL acetic anhydride solution of 2'-deoxy-1'β-piperonyl-3',5'-di-O-toluoyl-D-ribofuranose (1.40 g, 2.95 mmol), immersed in an ice-water bath, was added $Cu(NO_3)_2 \cdot 3H_2O$ (2.57 g, 9.38 mmol). The resulting solution was stirred for 25 min. The mixture was poured into 200 mL of a $NaHCO_3$ aqueous solution and extracted with ethyl acetate. The extract was washed with a saturated NaCl solution and dried over anhydrous $Na_2SO_4$. The product was purified by flash chromatography on silica gel with 18% ethyl acetate in hexane as the eluant. The product (1.38 g, 2.65 mmol) was obtained as a yellow oil (epimer α/β, 9:1)

at a yield of 90%. $^1$H NMR (300 MHz, CDCl$_3$, ppm, referenced to TMS at 0.00) δ 7.98 (2H, d, J=8.2Hz, Tol—H), 7.93 (2H, d, J=8.2 Hz, Tol—H), 7.54 (1H, s, Ar—H), 7.37 (1H, s, Ar—H), 7.27 (2H, d, J=8.0 Hz, Tol—H), 7.22 (2H, d, J=8.0 Hz, Tol—H), 6.09 (1H, d, J=6.6 Hz, CH$_2$), 6.08 (1H, d, J=6.6 Hz, CH$_2$), 5.77 (1H, dd, J=5.1, 10.2 Hz, H1'), 5.58 (1H, dd, J=1.8, 4.8 Hz, H3'), 4.72 (2H, m, H5'5"), 4.51 (1H, m, H4'), 2.94 (1H, ddd, J=1.2, 5.1, 6.4 Hz, H2'β), 2.43 (3H, s, CH$_3$), 2.40 (3H, s, CH$_3$), 2.05 (1H, m, H2'α); IR (CDCl$_3$ thin film, cm$^{-1}$), 2922, 2853, 1712, 1611, 1503, 1482, 1268, 1177, 1106; HRMS (FAB) m/z calcd for C$_{28}$H$_{25}$NO$_9$ 519.1529, found 519.1539.

2'-deoxy-1'β-nitropiperonyl-D-ribofuranose.

To a 30 mL methanol solution of 2'-deoxy-1'β-nitropiperonyl-3',5'-di-O-toluoyl-D-ribofuranose (0.22 g, 0.42 mmol), was added 0.5 M sodium methoxide in methanol (7.5 mL) and stirred for 45 min. The reaction was quenched by adding NH$_4$Cl powder, and then filtered and concentrated and flash chromatographed on silica gel with 8:2 ethyl acetate/hexane. The product was obtained as a yellow solid (0.12 g, 0.42 mmol) at a yield of 100%. UV(H$_2$O): λ$_{max}$=360.5 nm, ε (360.5 nm)=1.3×10$^4$, UV(CH$_3$OH): λhd max=346.0 nm, ε (346.0 nm)=1.4×10$^4$; mp 133–134° C.; $^1$H NMR (300 MHz, CDCl$_3$, ppm, referenced to TMS at 0.00) δ 7.54 (1H, s, Ar—H), 7.31 (1H, s, Ar—H), 6.12 (1H, d, J=3.0 Hz, CH$_2$), 6.11 (1H, d, J=3.0 Hz, CH$_2$), 5.68 (1H, dd, J=6.0, 9.0 Hz, H1'), 4.40 (1H, m, H3'), 4.02 (1H, m, H4'), 3.93 (2H, m, H5'5"), 2.63 (1H, ddd, J=3.0, 6.0, 8.9 Hz, H2'β), 1.92 (1H, m, H2'α); IR (CDCl$_3$ thin film, cm$^{-1}$), 3396 (br), 2931, 2857, 1520, 1504, 1482, 1329, 1255, 1033; HRMS (FAB) m/z calcd for C$_{12}$H$_{13}$NO$_7$ 283.0692, found 283.0686.

2'-deoxy-1'β-nitropiperonyl-5'-O-trityl-D-ribofuranose.

To 10 mL pyridine solution of 2'-deoxy-1'β-nitropiperonyl-D-ribofuranose (0.11 g, 0.39 mmol) and triethyl amine (0.15 mL) and N,N-dimethylaminopyridine (5 mg, 0.041 mmol), was added dimethoxytrityl chloride (0.194 mg, 0.50 mmol). After stirring for 6 hr, the reaction then poured in 50 mL of water and extracted with ethyl acetate. The extract was washed with a saturated NaHCO$_3$ solution, a saturated NaCl solution and dried over anhydrous Na$_2$SO$_4$. The product was obtained as yellow foam (0.16 g, 0.27 mmol) at a yield of 69% after flash chromatography on silica gel with 27.5% ethyl acetate in hexane as the eluant. $^1$H NMR (300 MHz, CDCL$_3$, ppm, referenced to TMS at 0.00) δ 7.55–7.19 (11H, m, Ar—H), 6.84 (4H, d, J=8.8 Hz), 6.09 (2×H, 2×d, J=8.4 Hz, CH$_2$), 5.69 (1H, dd, J=6.2, 8.8 Hz, H1'), 4.38 (1H, m, H3'), 4.06 (1H, m, H4'), 3.79 (6H, s, 2×OCH$_3$), 3.38 (2H, m, H5'5"), 2.62 (1H, ddd, J=3.1, 6.1, 9.3 Hz, H2'β), 1.96 (1H, m, H2'α); IR (CDCl$_3$ thin film, cm$^{-1}$), 2927, 1511, 1480, 1257, 1034; HRMS (FAB) m/z calcd for C$_{33}$H$_{31}$NO$_9$ 585.1998, found 585.1983.

2'-deoxy-1'β-nitropiperonyl-3'-O-phosphoramidite-5'-O-trityl-D-ribofuranose.

2'-deoxy-1'β-nitropiperonyl-5'-O-trityl-D-ribofuranose (60 mg, 0.103 mmol) was dissolved in 4 mL of CH$_2$CL$_2$ and 1 mL of triethyl amine, to which was added 2-cyanoethyl N,N-diisopropylchlorophosphoramidite (0.10 mL, 0.44 mmol).

After stirring for 3 hr, the solvent was removed under vacuum and the mixture was loaded to a silica gel column and eluted with 30% ethylacetate in hexane. The products were obtained as a light yellowish oil in two isomers (60 mg, 0.076 mmol) at a yield of 76%. $^1$H NMR (300 MHz, CDCl$_3$, ppm, referenced to TMS at 0.00) δ 7.55–7.20 (11H, m, Ar—H), 6.84 (4H, m), 6.10 (2H, m, CH$_2$), 5.67 (1H, m, H1'), 4.46 (1H, m), 4.21 (1H, m), 3.86 (1H, m), 3.80 (3H, s, OCH$_3$), 3.79 (3H, s, OCH$_3$), 3.62 (2H, m), 3.32 (1H, m), 2.78 (1H, m), 2.65 (2H, m, CH$_2$), 2.43 (2H, m, CH$_2$), 1.92 (1H, m), 1.17 (12H, d, J=6.8 Hz, 4×CH$_3$); $^{31}$P NMR (400 MHz, CDCl$_3$, ppm, referenced to TMP at 0.00) δ 149.24, 148.33; IR (CDCl$_3$ thin film, cm$^{-1}$), 2958, 2923, 2853, 1605, 1511, 1480, 1462, 1256, 1033; HRMS (FAB) m/z calcd for C$_{42}$H$_{48}$N$_3$O$_{10}$P 785.3077, found 785.3020.

2'-deoxy'1'β-nitropiperonyl-3'-O-toluoyl-D-ribofuranose.

To 7 mL pyridine solution of 2'-deoxy-1'β-nitropiperonyl-D-ribofuranose (0.15 g, 0.53 mmol) and triethyl amine (0.20 mL) and N,N-dimethylaminopyridine (6 mg, 0.049 mmol), was added dimethoxytrityl chloride (0.30 mg, 0.89 mmol). After stirring for 2 hr, extra dimethoxytrityl chloride (0.14 mg, 0.41 mmol) was added and the solution stirred for an additional 4 hr until the completion of tritylation. Toluoyl chloride (0.11 g, 0.72 mmol) was added to the reaction and stirred for another 6 hr. The mixture was poured into 20 mL of water and extracted with CH$_2$Cl$_2$.

The extract was washed with a saturated NaHCO$_3$ solution, a saturated NaCl solution and dried over anhydrous Na$_2$SO$_4$. After the solvent was removed, the residue was dissolved in 50 mL of 80% aqueous acetic acid and stirred overnight. After acetic acid was removed under vacuum, the residue was dissolved in 50 mL of water, and extracted with CH$_2$Cl$_2$. The extract was wished with a saturated NaHCO$_3$ solution, a saturated NaCl solution and dried over anhydrous Na$_2$SO$_4$. The product was obtained as a white-yellowish liquid (0.18 g, 0.46 mmol) at a total yield of 87% after flash chromatography on silica gel with 5% methanol in CH$_2$Cl$_2$ as the eluant. $^1$H NMR (300 MHz, CDCl$_3$, ppm, referenced to TMS at 0.00) δ 7.97 (2H, d, J=8.2 Hz, Tol—H), 7.54 (1H, s, Ar—H), 7.40 (1H, s, Ar—H), 7.27 (2H, d, J=7.9 Hz, Ar—H), 6.84 (4H, d, J=8.8 Hz), 6.12 (1H, d, J=2.7 Hz, CH$_2$), 6.11 (1H, d, J=2.7 Hz, CH$_2$), 5.71 (1H, dd, J=5.2, 10.0 Hz, H1'), 5.44 (1H, m, H3'), 4.22 (1H, dd, J=4.2, 7.3 Hz, H4'), 3.98 (2H, m, H5'5"), 2.89 (1H, ddd, J=1.8, 5.3, 7.0 Hz, H2'β), 2.43 (3H, CH$_3$), 2.04 (1H, ddd, J=6.8, 10.0, 13.8 Hz, H2'α); IR (CDCl$_3$ thin film, cm$^{-1}$), 2920, 2848, 1270, 1176, 1033; HRMS (FAB) m/z calcd for C$_{20}$H$_{19}$NO$_8$ 401.1110, found 401.1125.

2'-deoxy-1'β-nitropiperonyl-D-ribofuranose-5'-O-triphosphate.

2'-deoxy-1'β-nitropiperonyl-3'-O-toluoyl-D-ribofuranose (60 mg, 0.15 mmol) dried over P$_2$O$_5$ under vacuum in a desicator overnight was dissolved in 100 mL of pyridine and 750 mL of N,N-dimethyl formamide (DMF), to which was added freshly prepared 1 M 2-chloro-4H-1,3,2-benzodioxaphophin-4-one 0.25 mL and stirred for 20 min. 0.5 M Bis(tri-n-butylammonium) pyrophosphate in DMF (0.75 mL) followed by 0.13 mL of tri-n-butylamine were added and the mixture stirred for 20 min. To the mixture, was added 2 mL of 1% I$_2$ in pyridine/H$_2$O (98:2). After stirring for 15 min, excess I$_2$ was quenched by adding a few drops of NaHSO$_3$ solution. The mixture was vacuumed to dryness, then dissolved in 10 mL of methanol and 30 mL of concentrated ammonium hydroxide and kept at room temperature for 42 hr. After the solvent was removed, the aqueous portion was extracted with CH$_2$Cl$_2$. The aqueous layer was concentrated and purified by anion exchange chromatography with QA52 quaternary ammonium cellulose resin (Whatman). The column was elueated with 1400 mL of a NH$_4$HCO$_3$ solution (pH 9.4) in a linear gradient from 0.005–0.2 M. The collected fraction was concentrated by lyophilization and further purified on an HPLC reverse phase C-18 column with a linear gradient of 50 mm triethylammonium acetate (TEAA) in 0–25% acetonitrile.

Oligonucleotide Synthesis.

Oligonucleotides were synthesized on an Applied Biosystems 392 DNA/RNA synthesizer with standard phosphoramidite chemistry. An additional 10 min was given to the coupling step for incorporating modified nucleoside. The oligomers were purified by either HPLC or 12% polyacrylamide gel electrophoresis.

Melting Temperature.

Double stranded oligonucleotide 25-mers at concentration range of 1–20 μM, were dissolved in buffers of 100 mM NaCl, 10 mM sodium phosphate, pH 7.0. Quartz cuvetts with optical path-length of 1cm and 1 mm were used to measure the absorbance of the oligonucleotides in the range of 0.4–1.2 at 260 nm. An Aviv 62DS spectrophotometer was equipped with a heating program. The samples were heated from 40° to 75° C. at an increment of 0.52° C. per data point. Each data point was equilibrated for 30 sec with a maximum fluctuation of 0.1° C. The melting temperatures ($T_m$) were determined by taking the first derivatives of the melting curves (absorbance vs temperature). Thermodynamic data were calculated from a two state model.

Primer Extension Study.

The oligonucleotides were labelled by phosphorylation of the 5' terminal (4 pmol) with T4 polynucleotide kinase (10 unit) and [$\gamma$-$^{32}$P]ATP (7000 Ci/mmol, 166 μCi, 23 pmol) in 10 μL of 70 mM Tis-HCl, 10 mM $MgCl_2$, and 5 mM dithiothreitol (DTT), pH 7.6. The mixture was incubated at 37° C. for 2 hr and purified on a 8% denaturing polyacrylamide gel. Template (25-mer) and primer (11-mer) were annealed by heating to 65° C. and slowly cooling to room temperature. The complex (0.1 pmol) was mixed in 10 μL of DNA polymerase buffer (10 mM Tis-HCl, 5 mM $MgCl_2$, and 7.5 mM DTT, pH 7.5) with 100 μM individual deoxynucleoside triphosphate (dNTP). The primer extension was initiated by adding Klenow fragment of E. coli DNA polymerase I (1 unit) and incubated at 37° C. for 2 min and then quenched by adding 1 μL of 25 mM EDTA. The products were lyophilized and resuspended in 10 μL of formamide/dye and resolved on a 12% denaturing polyacrylamide gel. Electrophoresis was run under constant current of 25 mA after 30 min pre-running. The products on autoradiograph were quantified on a computing desitometer (Molecular Dynamics).

Photolysis.

5'-labelled oligonucleotide 25-mer (0.1 pmol) in 10 μL of 1×TE buffer (10 mM Tis-HCl, 1mM EDTA, pH 7.5) was irradiated at 350 nm in a Rayonet Photochemical Reactor. A Pyrex filter was used to cut off the light (<300 nm). A fan was used to keep photolysis close to room temperature. After photolysis at a fluence rate of 400 μW/cm$^2$ for 20 min, 90 μL of 1 M piperidine was added and heated to 90° C. for 30 min. The solvent was removed and the products were resuspended in 10 μL of formamide/dye and resolved on a 12% denaturing polyacrylamide gel.

Example 1

Synthesis of (Nitropiperonyl)deoxyriboside

A P★ base-containing nucleoside can be prepared by treatment of ditoluoylribosyl chloride (Hoffer, Chem. Ber. 93:2777 (1960)) with benzodioxol-4-yl Grignard giving a mixture of anomers in a 1:10 α:β ratio (87% yield). The mixture can be rectified by chromatography, giving the β anomer (76%), and the α anomer can be equilibrated with p-TsOH in toluene, giving a 1.5:1 mixture. $Cu(NO_3)_2/Ac_2O$ nitration (90% yield) yields 1 of FIG. 1.

Using conventional methods (see M. J. Gait, oligonucleotide Synthesis, IRC Press, Washington, D.C. (1984)), 1 of FIG. 1 can be converted to a 5'-dimethoxytrityl-3'-cyanoethyl(diisopropyl)phosphoramidite (2 of FIG. 1) and used in automated DNA synthesis. The Aphosphoramidite can be used to prepare the pentacosanucleotide 5 (see Table 1).

The hybridization properties of 5 can be compared against sequence 6 (see Table 1) and its single-base variants compared to the parent sequence 4 (see Table 1). Using known methods (Marky et al, Biopolymers 26:1601–1620 (1987)), the thermodynamics of melting can be determined with several different base pairs in the boxed region (see the results summarized in Table 1—SEQ ID NO:1 to SEQ ID NO:3). These data indicate that P★ is a good T mimic, but also show that it also pairs reasonably well with G and A. However, a P★-C mismatch is even more destabilizing than a T—T mismatch.

TABLE 1

| | |
|---|---|
| 5'-GTA GAA TTC TTT TCC TTC TAG ATC G-3' | 4 |
| 5'-GTA GAA TTC TTT PCC TTC TAG ATC G-3' | 5 |
| 3'-CAT CTT AAG AAA AGG AAG ATC TAG C-5' | 6 |
| GG AAG ATC TAG-5' | 7 |

| Base Pair | ΔH* (kcal/mol) | ΔS* (kcal/mol · K) | ΔG* (kcal/mol) |
|---|---|---|---|
| T-A | −195.9 | −0.5548 | −30.5 |
| P*-A | −187.7 | −0.5382 | −27.2 |
| P*-T | −163.9 | −0.469 | −24.1 |
| P*-G | −154.4 | −0.440 | −23.2 |
| P*-C | −143.1 | −0.408 | −21.5 |
| T-T | −145.6 | −0.412 | −22.7 |

Example 2

Use of P★ base in Primer Extension

Figure 2:
FIG. 2 shows extension products obtained using primer 7 and template 5.
Figure 2:
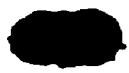
Figure 2:
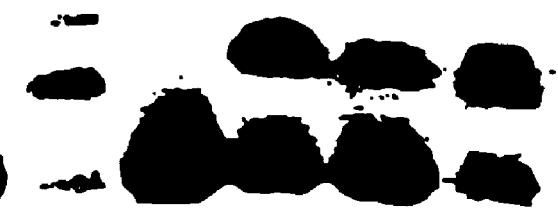
Figure 3:
FIG. 3 shows fragments resulting from irradiation of a P★ base-containing oligonucleotide.
Figure 3:

The ability of the P★ base to support primer extension reactions was studied. Using 5'-end-labeled primer 7 (see Table 1—SEQ ID NO:4) and template 5 (see Table 1) with E. coli DNA polymerase I or Klenow DNA polymerase and relatively high concentrations (100 μM) of single dNTPs, extension products were obtained with G, C, and T (see FIG. 2). Primer 7 (see Table 1) was fully extended in the presence of all four dNTPs even at ordinary concentrations. The resulting duplex was end-labeled and subjected to irradiation at 350 nm, followed by base treatment (piperidine, 95° C. or $K_2CO_3$). Analysis of the resulting oligonucleotide fragments suggested that the product was an 12-mer bearing a 3'-phosphate (see FIG. 3).

The P★ base-containing nucleoside was converted to triphosphate 3 (FIG. 1) using salicylchlorophosphite (Ludwig et al, Org. Chem. 54:631 (1989)) and used in primer extension with primer 7 (see Table 1) and template 4 (see Table 1). The production of exclusively a pentadecanucleotide shows that the polymerase can incorporate this unnatural base as the incoming triphosphate opposite Ts.

Example 3

Synthesis of Photocleavable Nucleoside Triphosphate

A modified nucleotide of the invention can be expected to have application in high throughput screening and sequencing of larger DNA populations using DNA chip technologies such as APEX (Arrayed Primer EXtension). Characteristics of modified nucleotides suitable for use in such technologies include recognition of the nucleotide by DNA polymerase, specificity and predictable strand cleavage. DNA polymerase recognizes the modified nucleoside triphosphate as a substrate or DNA building block similar to the naturally occurring nucleoside triphosphates. The polymerase specifically places the modified nucleotide opposite only one, or predominantly one, of the naturally occurring nucleotides. Predictable strand cleavage is obtained when the DNA containing the modified nucleotide is irradiated with light.

A modified nucleotide of the present invention, a nitropiperonyl deoxyriboside (P)

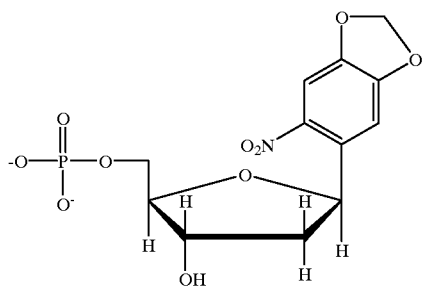

mimics thymidine in size and shape. The photocleavable moiety is a methylenedioxy-nitrobenzene group cleaved by light of 350 nm. When the modified nucleotide is incorporated into a DNA strand, Klenow fragment DNA polymerase places natural nucleoside triphosphates opposite the modified nucleotide. Moreover, there is specificity in this placement, with dATP being incorporated opposite the modified nucleotide more than the other nucleotide triphosphates. Two of the other natural nucleotide triphosphates, dGTP and dTTP, are incorporated much less than dATP. The dCTP is not incorporated at all. Further studies have focused on assessing the cleavage characteristics of the P-base-containing DNA and on the specificity with which the DNA polymerase recognizes and reacts with the modified P nucleotide.

The synthesis of the target photocleavable nucleotide triphosphate, dPTP, is described below. First, 1'α-chloro-3', 5'-di-O-toluoyl-2'-deoxyribose was prepared from deoxy-D-ribose according to Hoffer et al as shown in Scheme 1. Deoxy-D-ribose was treated with HCl and methanol to generate the methoxy derivative 2 at the anomeric center. Compound 2 was then treated with toluoyl chloride and pyridine to provide the di-protected Compound 3. The methoxy group was replaced with a choride by treatment of 3 with HCl gas.

Scheme 1
Synthesis of 1' α-chloro-3', 5'-di-O-toluoyl-2'-deoxyribose

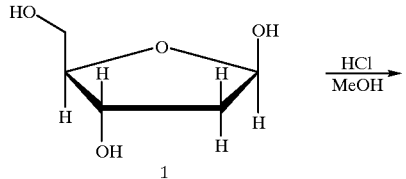

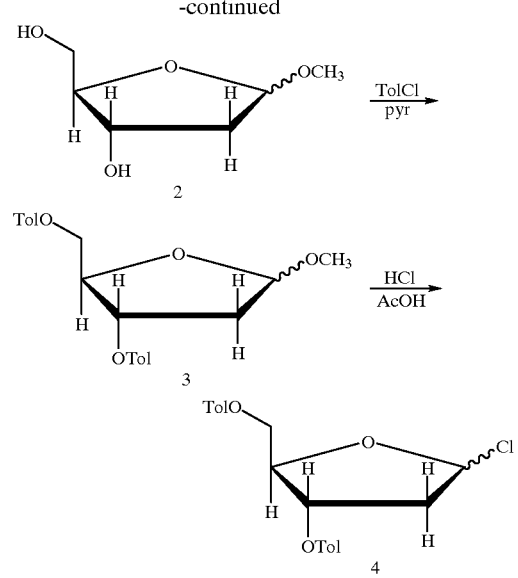

The triphosphate P was synthesized by the route shown in Scheme 2. The Grignard reagent of 4-bromo-1,2-methylenedioxybenzene was generated by treatment with $Mg^0$ and $CdCl_2$ in THF. This Grignard reagent was allowed to react with Compound 4 to provide the coupled product as a mixture of anomers. The mixture of products was allowed to epimerize by refluxing in toluene for 2 hours, providing predominantly the β-anomer. The anomers were separated by column chromatography and the β-anomer was carried on throughout the remainder of the synthesis. Compound 5 was treated with copper nitrate and acetic anhydride to generate the nitrobenzene derivative 6. The toluoyl groups were then removed by treatment with sodium methoxide in methanol. The triphosphate group was added to the 5' position of the ribose ring by sequential treatment of 7 with 2-chloro-4H-1,2,3-benzodioxaphophin-4-one, bis(tri-n-butyl ammonium) pyrophosphate and iodine. The resulting triphosphate P was purified by anion exchange chromatography and HPLC.

Scheme 2
Synthesis of triphosphate P

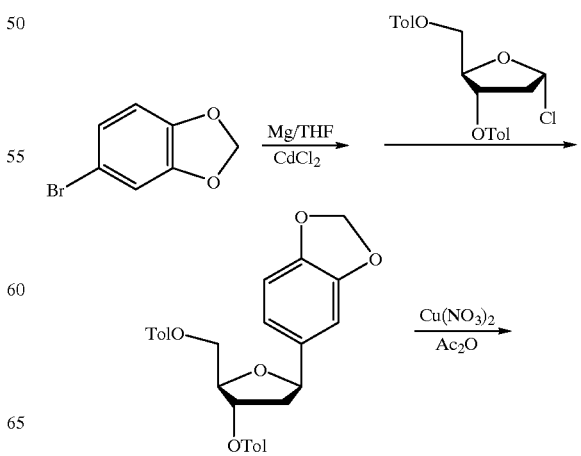

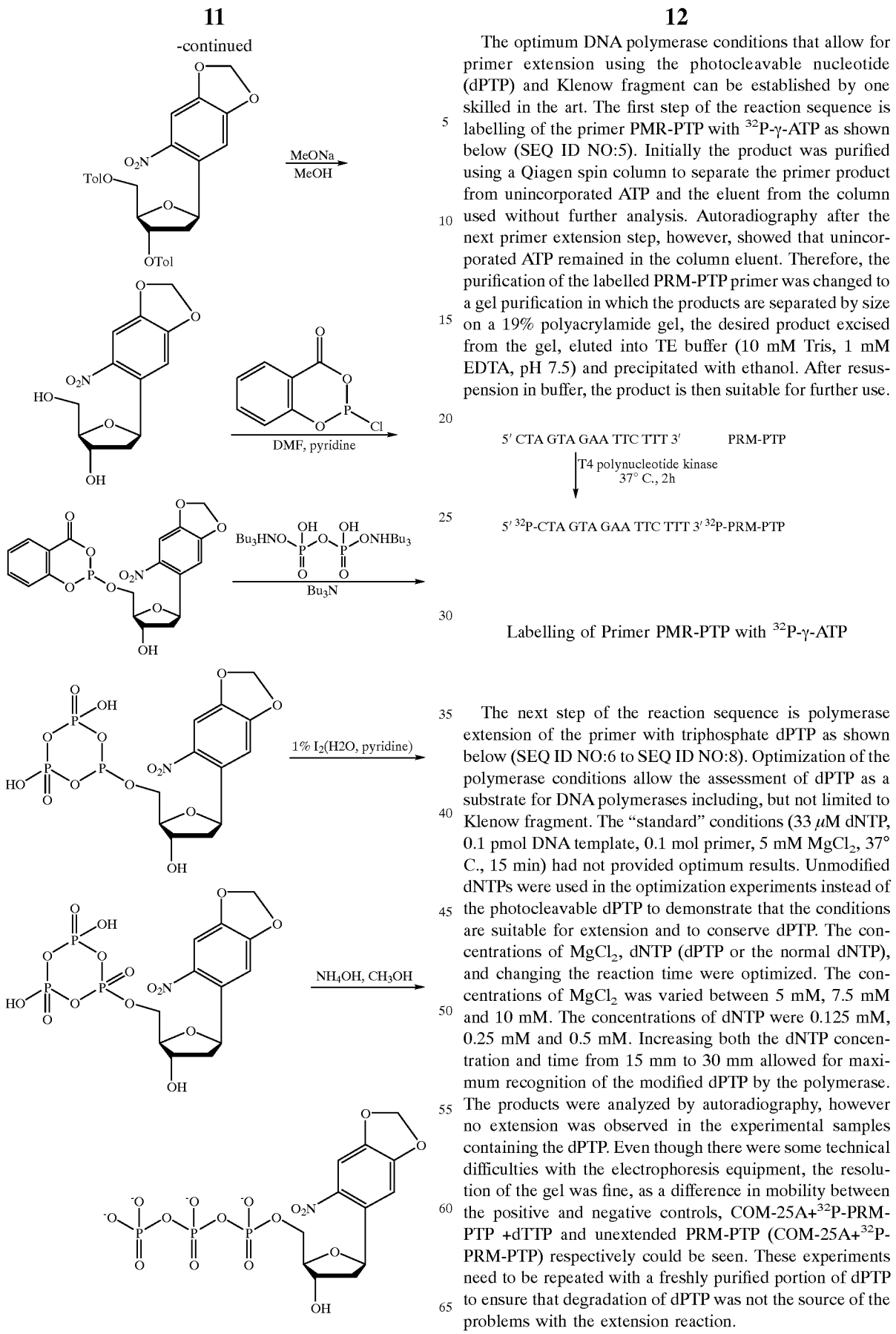

The optimum DNA polymerase conditions that allow for primer extension using the photocleavable nucleotide (dPTP) and Klenow fragment can be established by one skilled in the art. The first step of the reaction sequence is labelling of the primer PMR-PTP with $^{32}$P-γ-ATP as shown below (SEQ ID NO:5). Initially the product was purified using a Qiagen spin column to separate the primer product from unincorporated ATP and the eluent from the column used without further analysis. Autoradiography after the next primer extension step, however, showed that unincorporated ATP remained in the column eluent. Therefore, the purification of the labelled PRM-PTP primer was changed to a gel purification in which the products are separated by size on a 19% polyacrylamide gel, the desired product excised from the gel, eluted into TE buffer (10 mM Tris, 1 mM EDTA, pH 7.5) and precipitated with ethanol. After resuspension in buffer, the product is then suitable for further use.

5' CTA GTA GAA TTC TTT 3'   PRM-PTP

| T4 polynucleotide kinase
| 37° C., 2h

5' $^{32}$P-CTA GTA GAA TTC TTT 3' $^{32}$P-PRM-PTP

Labelling of Primer PMR-PTP with $^{32}$P-γ-ATP

The next step of the reaction sequence is polymerase extension of the primer with triphosphate dPTP as shown below (SEQ ID NO:6 to SEQ ID NO:8). Optimization of the polymerase conditions allow the assessment of dPTP as a substrate for DNA polymerases including, but not limited to Klenow fragment. The "standard" conditions (33 μM dNTP, 0.1 pmol DNA template, 0.1 mol primer, 5 mM MgCl$_2$, 37° C., 15 min) had not provided optimum results. Unmodified dNTPs were used in the optimization experiments instead of the photocleavable dPTP to demonstrate that the conditions are suitable for extension and to conserve dPTP. The concentrations of MgCl$_2$, dNTP (dPTP or the normal dNTP), and changing the reaction time were optimized. The concentrations of MgCl$_2$ was varied between 5 mM, 7.5 mM and 10 mM. The concentrations of dNTP were 0.125 mM, 0.25 mM and 0.5 mM. Increasing both the dNTP concentration and time from 15 mm to 30 mm allowed for maximum recognition of the modified dPTP by the polymerase. The products were analyzed by autoradiography, however no extension was observed in the experimental samples containing the dPTP. Even though there were some technical difficulties with the electrophoresis equipment, the resolution of the gel was fine, as a difference in mobility between the positive and negative controls, COM-25A+$^{32}$P-PRM-PTP +dTTP and unextended PRM-PTP (COM-25A+$^{32}$P-PRM-PTP) respectively could be seen. These experiments need to be repeated with a freshly purified portion of dPTP to ensure that degradation of dPTP was not the source of the problems with the extension reaction.

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 1
gtagaattct tttccttcta gatcg                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:Primer
<221> NAME/KEY: modified_base
<222> LOCATION: (13)
<223> OTHER INFORMATION: N = photocleavable base

<400> SEQUENCE: 2
gtagaattct ttnccttcta gatcg                                              25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 3
cgatctagaa ggaaaagaat tctac                                              25

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence:Primer

<400> SEQUENCE: 4
gatctagaag g                                                             11

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:Primer

<400> SEQUENCE: 5
ctagtagaat tcttt                                                         15

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:Primer
<221> NAME/KEY: misc_feature
<222> LOCATION: (12)
<223> OTHER INFORMATION: N = A, G, C or T

<400> SEQUENCE: 6

```
cgatctagag gnaaagaatt ctac                                              24
```

```
<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 7
ctagtagaat ttctttt                                                      16

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:Primer
<221> NAME/KEY: misc_feature
<222> LOCATION: (17)
<223> OTHER INFORMATION: N = A, G, C or T

<400> SEQUENCE: 8
ctagtagaat ttcttn                                                       17
```

5' CG ATC TAG AGG XAA AGA ATT CTA C 3'          COM-25X

3' TT TCT TTA AGA TGA TC-$^{32}$P 5'            $^{32}$P-PRM-PTP

↓ Klenow fragment, dNTP

5' CG ATC TAG AGG XAA AGA ATT CTA C 3'

3' YTT TCT TTA AGA TGA TC-$^{32}$P 5'

X = A, C, G, or T
Y = T, G, C, or A
Extension Reaction
* * *

All documents cited above are hereby incorporated in their entirety by reference.

One skilled in the art will appreciate from a reading of this disclosure that various changes in form and detail can be made without departing from the true scope of the invention.

What is claimed is:

1. A compound of formula I

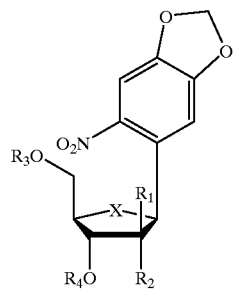

wherein $R_1$ is —H and $R_2$ is —H, —OH or —OY, wherein Y is $C_{1-4}$ alkyl, $R_3$ and $R_4$ are, independently, —H, a protecting group, or a mono-, di- or triphosphate, and X is O or S.

2. A compound comprising the moiety of formula II

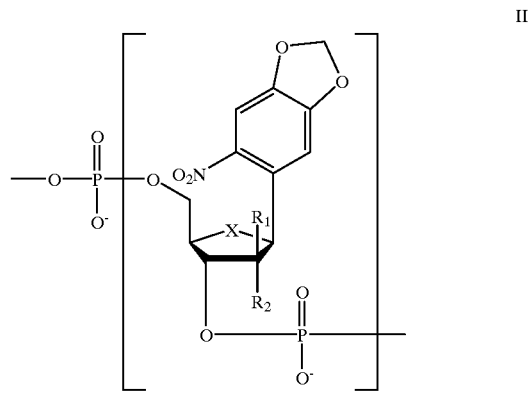

wherein $R_1$ is —H and $R_2$ is —H, —OH or —OY wherein Y is $C_{1-4}$ alkyl, and X is O or S.

3. The compound according to claim 2 wherein said compound is an oligonucleotide.

4. A method of synthesizing a nucleic acid susceptible to site specific cleavage comprising:

reacting a compound of the formula
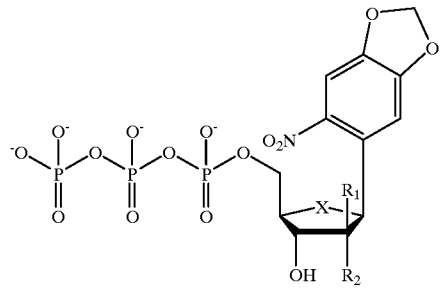
wherein $R_1$ is —H and $R_2$ is —H, —OH or —OY, wherein Y is $C_{1-4}$ alkyl, and X is O or S,
with an oligonucleotide under conditions such that a nucleic acid comprising a moiety of the formula
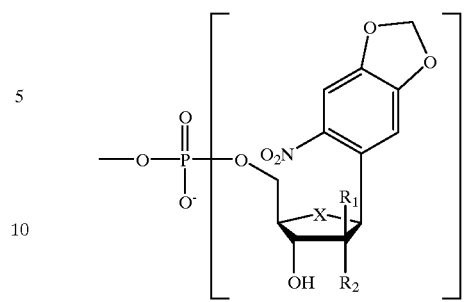
is produced, said nucleic acid being susceptible to site specific cleavage.
* * * * *